(12) United States Patent
Hönicke et al.

(10) Patent No.: US 6,392,065 B1
(45) Date of Patent: May 21, 2002

(54) METHOD OF PRODUCING EPOXY RESINS BY GAS PHASE EPOXIDATION

(75) Inventors: Dieter Hönicke, Karlsruhe; Viorel Duma, Chemnitz; Waldemar Krysmann, Föha, all of (DE)

(73) Assignee: Creavis Gesellschaft fuer Technologie und Innovation mbH, Marl (DE)

( * ) Notice: Subject to any disclaimer, the term of this patent is extended or adjusted under 35 U.S.C. 154(b) by 0 days.

(21) Appl. No.: 09/582,632

(22) PCT Filed: Nov. 25, 1999

(86) PCT No.: PCT/EP99/09131

§ 371 Date: Jul. 26, 2000

§ 102(e) Date: Jul. 26, 2000

(87) PCT Pub. No.: WO00/31056

PCT Pub. Date: Jun. 2, 2000

(30) Foreign Application Priority Data

Nov. 26, 1998 (DE) .......................... 198 54 615

(51) Int. Cl.⁷ .......................................... C07D 301/03
(52) U.S. Cl. ........................................ 549/523
(58) Field of Search ........................... 549/523

(56) References Cited

FOREIGN PATENT DOCUMENTS

| DE | 198 54 615 A | * | 7/1999 |
|----|---|---|---|
| WO | 97/34693 | * | 9/1997 |
| WO | WO 98/00413 | | 1/1998 |
| WO | WO 98/00414 | | 1/1998 |
| WO | WO 98/00415 | | 1/1998 |
| WO | WO 98/30552 | | 7/1998 |

OTHER PUBLICATIONS

Derwent Publication No. XP002134156, Apr. 15, 1994.*
Chemical Abstract No. XP002134155, Jun. 26, 1999.*
Cited in Int. Search Report.*
N. Calamur, et al., "Propylene Oxide", *Kirk–Othmer Encyclopedia of Chemical Technology*, 1996, vol. 20, 4th Edition, Wiley & Sons, New York, pp. 270–303.
K. Weissermel, et al., "Oxidationsprodukte des Ethylens", *Industrielle Organische Chemie*, 1998, pp. 158–169.
D. Kahlich, et al., "Propylene Oxide", *Ullmanns's Encyclopedia of Industrial Chemistry*, 1993, vol. A22, pp. 239–261.

* cited by examiner

Primary Examiner—T. A. Solola
(74) Attorney, Agent, or Firm—Oblon, Spivak, McClelland, Maier & Neustadt, P.C.

(57) ABSTRACT

The invention relates to a method of producing epoxy resins from hydrocarbons with olefinic double bonds, especially alkenes, by heterogeneous catalyzed oxidation in the gaseous phase. According to said method, and oxidic solid catalyst is released which contains iron as its active component at a concentration of 0.001–1% and alkali and/or alkaline earth elements as the promoters. $N_2O$ is used as the oxidizing agent. The granulated oxidic solid catalyst, especially on the basis of $SiO_2$ as the carrier, has a specific surface of greater that 50 $m^2/g$. The ratio of the concentrations of the active components to the promoter components is preferably between 1:100 and 10:1. The partial oxidation of hydrocarbons with olefinic double bonds, especially propene, results in propene selectivities of 10–70% at reaction temperatures of 300–500° C. and conversions of 2–30%. The catalyst repeatedly used in the reaction process can easily be regenerated by oxidation in air so that it retains its high activity even after 50 or more regeneration cycles.

6 Claims, No Drawings

METHOD OF PRODUCING EPOXY RESINS BY GAS PHASE EPOXIDATION

THIS APPLN. IS A 371 OF PCT/EP99/0913 FILED Nov. 25, 1999.

FIELD OF THE INVENTION

The invention relates to a process for the preparation of epoxides by gas-phase oxidation of hydrocarbons having olefinic double bonds by means of a reaction under heterogeneous catalysis, which process can be used in particular in the chemical industry.

PRIOR ART

It is known that the oxidation of ethene to ethene oxide is carried out industrially virtually exclusively in the gas phase. The industrial catalysts used contain silver as the active component and optionally further promoters and activators, such as, for example, Cs, Ba or K [K. Weissermel and H.-J. Arpe, Industrielle Organische Chemie [Industrial Organic Chemistry], 5th Edition, VCH Verlag, Weinheim, 1998, pages 159–165]. The gas-phase oxidation of propene or other alkenes which have methylene or methyl groups in the α position leads only to very low epoxide selectivities over these or similar catalysts at an economical alkene conversion. For this reason, propene oxide is currently prepared by an indirect route in the liquid phase, in particular by the chlorohydrin process or by oxidation with hydroperoxides. However, the chlorohydrin process leads to large chlorine losses in the form of useless $CaCl_2$ or NaCl solutions, which pollute the environment. The oxidation with hydroperoxides leads to large amounts of coproducts, such as, for example, styrene or tert-butanol, which adversely affect the economy of the process [Industrielle Organische Chemie (Industrial Organic Chemistry), ibid., pages 291–297; Ullmann's Encyclopedia of Industrial Chemistry, 5th ed., VCH Verlag, Weinheim, 1993, Vol. A22, pages 23–251; Kirk-Othmer Encyclopedia of Chemical Technology, 4th ed., John Wiley & Sons, New York, 1996, Vol. 20, pages 271–287]. At present, there is no industrial process for the direct oxidation of propene to propene oxide in the gas phase. Olin (USA) operates a pilot plant for the direct oxidation of propene, which is catalyzed by a lithium nitrate melt. In this technically complicated process, relatively large amounts of different byproducts, such as, for example, methanol, acetaldehyde, carbon dioxide and carbon monoxide, are formed in addition to propene oxide [Industrielle Organische Chemie (Industrial Organic Chemistry), ibid., page 300; Ullmann's Encyclopedia of Industrial Chemistry, ibid., page 251; Kirk-Othmer Encyclopedia of Chemical Technology, ibid., page 288]. The patent WO 98/30552 describes a process for the oxidation of propene over a silver/gold catalyst. A disadvantage of the invention is that a propene oxide selectivity of 50% is possible only at low propene conversions of 2%. A further disadvantage of this invention is the use of large amounts of carbon dioxide as a promoter for the reaction (the recommended concentration in the starting gas is stated as 5–25%). The patents WO 98/00413, WO 98/00414 and WO 98/00415 describe processes for the oxidation of propene in the gas phase over a gold catalyst. A disadvantage of the invention is that only low yields of propene oxide can be achieved. A further disadvantage of the inventions is also that the cost-efficiency of the process is adversely affected by the use of an expensive catalyst.

AIM OF THE INVENTION

The aim of the invention is to eliminate the disadvantages described and to develop a technologically simple process which permits the partial oxidation of hydrocarbons having olefinic double bonds under heterogeneous catalysis to give epoxides with relatively high conversions and selectivities, the catalyst used being distinguished by high long-term activity and stability, abrasion resistance and capability of being regenerated.

SUMMARY OF THE INVENTION

It is the object of the invention to develop a process which, through the use of an economical solid catalyst and a gaseous oxidizing agent, leads to the epoxidation of hydrocarbons having olefinic double bonds, in particular alkenes, such as, for example, propene, in the gas phase with high epoxide selectivities.

According to the invention, the object is achieved if the solid catalyst is based on an oxide support, in particular silica ($SiO_2$), iron oxide is present as an active component and synergistic elements from Group 1 and/or Group 2 of the Periodic Table of the Elements are present as promoters. The fact that the active component having an iron content of between 0.001% and 1% is uniformly and homogeneously distributed on and/or in the support and the carrier has a specific surface area of more than $50 m^2/g$ has been found to be advantageous. Furthermore, it is advantageous if the promoter, in particular sodium ions, is applied by impregnation of the $SiO_2$ matrix, which already contains active component, up to a concentration of 1% and the "green" catalyst thus prepared is made ready for use by calcination at a temperature between 300 and 1000° C. It was found that a pure or an Na ion-promoted oxide support, in particular $SiO_2$, has no or only very little activity and selectivity for the epoxidation of hydrocarbons having olefinic double bonds and, according to the invention, the presence of iron on and/or in the matrix of the oxide support, in particular $SiO_2$, is decisive for the catalytic activity and selectivity in the epoxidation reaction.

When the catalyst thus prepared is used in a flow apparatus, nitrous oxide in concentrations of 5% to 99% is used, according to the invention, for the oxidation. For example, nitrogen, helium or alkane is used as an inert gas. The reaction is carried out in a temperature range of 300–500° C. at space velocities of 1–20 $[h^{-1}g_{Cat}^{-1}$, so that, according to the invention, the epoxide selectivity is between 10 and 70% at conversions of 2–30%. It is advantageous that the catalyst according to the invention loses its activity only to an insignificant extent during the reaction, so that it needs to be reactivated by "burning off" in air or in another oxygen-containing gas only after an oxidation time of 5–20 h. Also remarkable is the fact that the catalyst is highly active, mechanically stable and abrasion-resistant even after more than 50 reactivation cycles.

The invention is to be explained below in 6 examples.

EXAMPLE 1 commercial silica gel having an Fe content of 0.0100% and a specific surface area of 484 $m^2/g$ was impregnated for 48 h with a $10^{-3}$ mol/l sodium acetate-containing aqueous solution with occasional stirring. After filtration and washing with distilled water, the silica gel impregnated with Na ions was calcined in the first stage for 5 h at 600° C. In the second stage, the catalyst was additionally calcined for 6 h at 700° C.

The catalyst thus prepared was used for the oxidation reaction in a flow apparatus in a quartz tubular reactor. The reaction products were determined and quantified on-line by gas chromatography and IR photometry. With a starting material stream composition of 1% of propene, 15% of $N_2O$ and 84% of He and a space velocity of 2 $l \cdot h^{-1} \cdot g_{Cat}^{-1}$, a propene conversion of 11% and a propene oxide selectivity of 18% were determined after an operating time of 80 min at a reaction temperature of 400° C. The byproducts consisted mainly of propanal, acetone, acrolein and oxides of carbon.

EXAMPLE 2

A commercial silica gel having an Fe content of 0.0080% and a specific surface area of 309 m²/g was impregnated with a 10$^{-3}$ molar aqueous sodium acetate solution for 48 h at room temperature with occasional stirring. After filtration and washing with distilled water, the filter cake was dried and was calcined in the first stage for 5 hours at 5000° C. In the second calcination stage, the catalyst was treated for 6 hours at 800° C. The catalyst thus prepared was used in the quartz reactor of the flow apparatus according to Example 1 and tested under the same conditions as in Example 1. It was found that a propene conversion of 4.5% is achieved, and the propene oxide selectivity increased to 23%. Mainly propanal, acetone, acrolein and oxides of carbon were formed as byproducts.

EXAMPLE 3

A commercial silica gel having an Fe content of 0.0006% was impregnated with an Fe(III) acetylacetonate-containing toluene solution by the "incipient wetness" method, so that the Fe content of the sample after the calcination (5 h at 600° C.) reaches 0.0100%. This catalyst was then promoted with Na ions by the method described in Example 1.

After calcination for 6 hours at 700° C., the catalyst was used in the flow apparatus for the oxidation reaction, according to Example 1. With a starting material stream composition of 1% of propene, 15% of $N_2O$ and 84% of He and a space velocity of 2 $l \cdot h^{-1} \cdot g_{Cat}^{-1}$, a propene conversion of 5% and a propene oxide selectivity of 60% were determined at 350° C. after an operating time of 130 min. With the same starting material composition and space velocity, conversions of 8.7 and 6.0 and 4.3%, respectively, and selectivities of 49.6 and 51.8 and 48.1%, respectively, were determined at 375° C. after an operating time of 130 min and 330 min and 680 min. In a second experiment, carried out under the same last-mentioned conditions but after "burning off" of the catalyst in air at 520° C., conversions of 8.3 and 6.0 and 4.2%, respectively and selectivities of 50.5, 51.7 and 48.9%, respectively, were determined for the same operating times. The byproducts correspond to those of Example 1.

EXAMPLE 4

A silica sol was prepared from tetraethyl orthosilicate (0.3 mol), ethanol (1.95 mol), isopropanol (0.3 mol), 1-dodecylamine (0.09 mol) and water (10.8 mol) and was left to gel for 48 h at room temperature. The chemically pure silica gel having a specific surface area of 1167 m²/g was obtained by drying and calcination for 5 hours at 600° C. The silica gel was enriched, as in Example 3, with an amount of Fe up to an Fe concentration of 0.0100% and then promoted with Na ions. After calcination for 6 hours at 700° C., the catalyst was used in the reaction apparatus, according to Example 1. At a starting material stream composition of 1% of propene, 40% of $N_2O$ and 59% of He and a space velocity of 2 $l \cdot h^{-1} \cdot g_{Cat}^{-1}$, a propene conversion of 5% and a propene oxide selectivity of 44% were determined at 375° C. after an operating time of 51 min. The byproducts correspond to those of Example 1.

EXAMPLE 5

A commercial mixed oxide catalyst support comprising 97% of $SiO_2$ and 3% of $TiO_2$ was impregnated according to Example 3 with an Fe(III) acetylacetonate-containing toluene solution by the "incipient wetness" method, so that the Fe content after the calcination (5 h at 600° C.) reaches 0.03%. This catalyst was then treated with a $10^{-1}$ mol/l sodium acetate-containing aqueous solution by the method described in Example 1, filtered, washed, and calcined for 6 hours at 700° C. The iron oxide-containing catalyst thus prepared, having a BET surface area of 193 m²/g, showed a propene conversion of 5.6% and a propene oxide selectivity of 7.7% in the flow apparatus with a starting material stream composition according to Example 1 and a space velocity of 4 $l \cdot h^{-1} \cdot g_{Cat}^{-1}$ at a reaction temperature of 400° C. after an operating time of 76 minutes. Mainly propanal, acetone, acrolein and oxides of carbon were formed as byproducts.

EXAMPLE 6

A commercial silica gel having an Fe content of 0.0006% was impregnated with an Fe(III) acetylacetonate-containing toluene solution by the "incipient wetness" method, so that the Fe content of the sample after the calcination (5 h at 600° C.) reaches 0.03%. This catalyst was then treated with a 0.1 mol/l sodium acetate-containing aqueous solution by the method described in Example 1, filtered, washed, and calcined for 6 h at 700° C. The catalyst was used for the partial oxidation of 1-butene in a flow apparatus according to Example 1. With a starting material stream composition of 1-butene, 15% of $N_2O$ and 84% of He and a space velocity of 4 $l \cdot h^{-1} \cdot g_{Cat}^{-1}$, a butene conversion of 28.8% and 23.8%, respectively, and a butene oxide selectivity of 14.1% and 15.7%, respectively, are determined after an operating time of 76 min and 127 min, respectively, at a reaction temperature of 400° C. About 5% of oxides of carbon are also formed in addition to about 80% of organic byproducts.

What is claimed is:

1. A process for the preparation of epoxides by gas-phase oxidation of hydrocarbons having olefinic double bonds by means of a reaction under heterogeneous catalysis, which comprises oxidizing the hydrocarbons having olefinic double bonds with $N_2O$ over an iron-containing solid oxide catalyst.

2. The process according to claim 1, wherein the oxidation agent $N_2O$ is used in concentrations of 5–99%, at reaction temperatures of 300–500° C., and spacial velocities of 1–20 $l \cdot h^{-1} \cdot g_{cat}^{-1}$, and wherein a degree of conversion of 2–30% is adjusted.

3. The process as claimed in claims 1, wherein the oxide catalyst has an iron content between 0.0001% and 1%.

4. The process according to claim 1, wherein the catalyst is promoted with one or more synergetically complementary elements from Group 1 and/or Group 2 of the periodic system of elements, wherein the promotor content is between 0.001% and 1%, and wherein a concentration ratio to the iron content of 1:10 to 100:1 is achieved.

5. The process as claimed in any of claims 1, wherein the iron-containing oxide catalyst is based on silica gel.

6. The process as claimed in any of claims 1, wherein the hydrocarbon having an olefinic double bond is propylene.

* * * * *